United States Patent [19]

Yamamoto

[11] Patent Number: 4,464,383
[45] Date of Patent: Aug. 7, 1984

[54] IMMUNOMODULATOR CONTAINING TRITHIAZOLE PENTAMETHINE CYANINE DERIVATIVE

[76] Inventor: Itaru Yamamoto, No. 1-102, Kikyo-machi, Hanajiri, Okayama-shi, Okayama-ken, Japan

[21] Appl. No.: 404,843

[22] Filed: Aug. 3, 1982

[30] Foreign Application Priority Data

Nov. 24, 1981 [JP] Japan .................................. 56-188610
Jun. 14, 1982 [JP] Japan .................................. 57-102393

[51] Int. Cl.³ .......................................... A61U 31/425
[52] U.S. Cl. ..................................................... 424/270
[58] Field of Search ........................................ 424/270

*Primary Examiner*—Stanley J. Friedman
*Attorney, Agent, or Firm*—Armstrong, Nikaido, Marmelstein & Kubovcik

[57] ABSTRACT

A pharmaceutical composition useful as immunomodulator comprising an effective amount of a trithiazole pentamethine cyanine derivative having the following general formula (I):

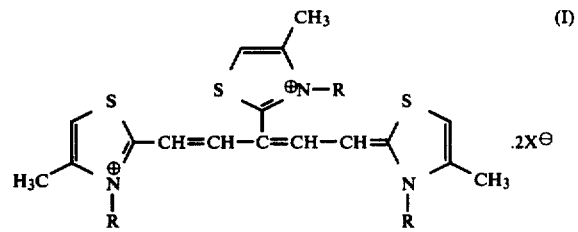

wherein R is an alkyl group having 1 to 15 carbon atoms, and X is a halogen atom, or a residual group of perchloric acid, nitric acid or an organic acid. The composition is useful for the prevention and treatment of various types of immune diseases, particularly rheumatoid arthritis.

9 Claims, 10 Drawing Figures

IMMUNOMODULATOR CONTAINING TRITHIAZOLE PENTAMETHINE CYANINE DERIVATIVE

BACKGROUND OF THE INVENTION

The present invention relates to a novel pharmaceutical composition useful as immunomodulator, and more particularly to a pharmaceutical composition containing a trithiazole pentamethine cyanine derivative as an effective ingredient, which is useful for the prevention and treatment of various types of immune diseases, particularly rheumatoid arthritis.

Recently, there have been developed various immunomodulators such as Levamisole, D-penicillamine and CCA[N-(2-carboxyphenyl)-4-chloroanthranilic acid disodium salt]. However, these immunomodulators are not necessarily satisfiable due to defects such as severe toxicities.

SUMMARY OF THE INVENTION

It is an object of the present invention to provide an immunomodulator which possesses an excellent immunomodulating action but does not possess any severe toxicity and side-effect.

The present invention provides a pharmaceutical composition useful as immunomodulator comprising an effective amount of a trithiazole pentamethine cyanine derivative having the following general formula (I):

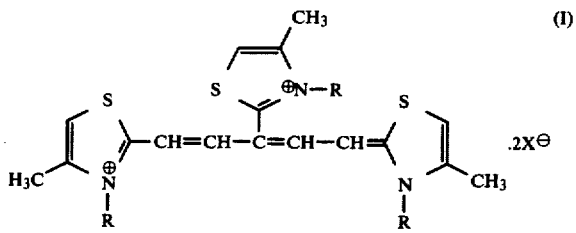

wherein R is an alkyl group having 1 to 15 carbon atoms, and X is a halogen atom, or a residual group of perchloric acid, nitric acid or an organic acid.

DETAILED DESCRIPTION

Figure 1:
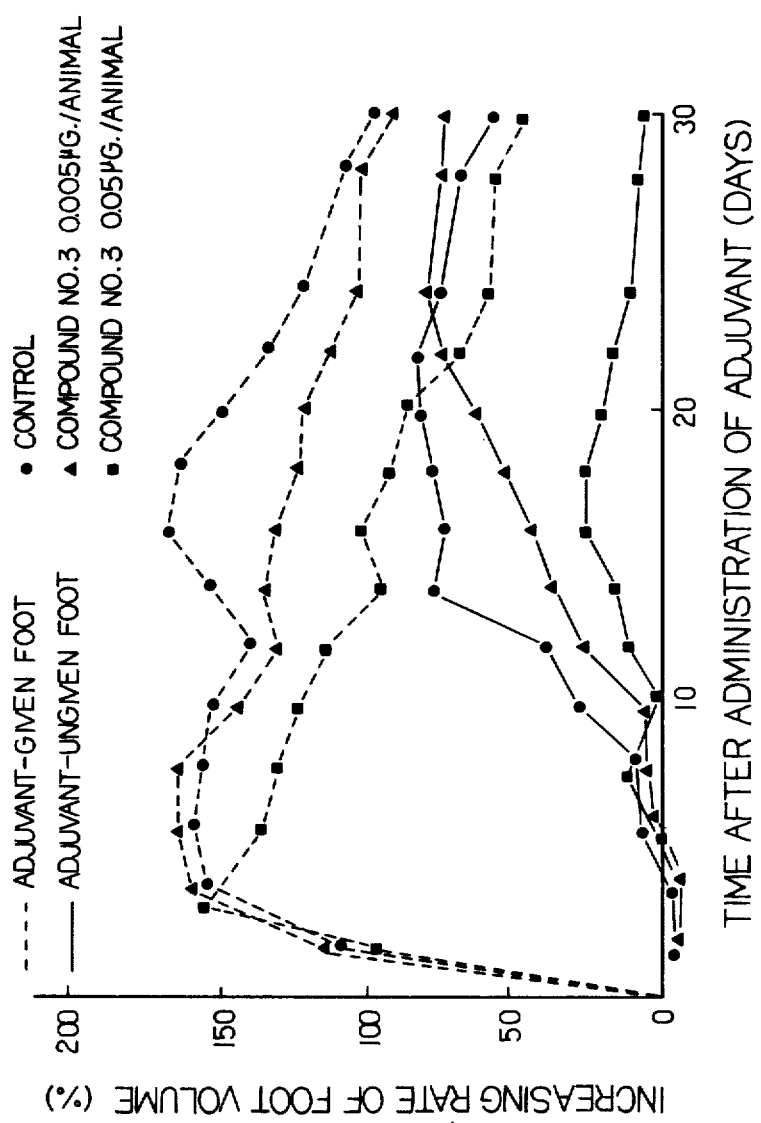
FIGS. 1 and 2 are graphs showing the preventive effect of the instant immunomodulator on adjuvant arthritis in rat.

Among the compounds having the general formula (I), the compound wherein R is a n-heptyl and X is iodine is a known compound called "Platonin". It has been known that Platonin possesses pharmacological activities such as antibacterial activity, the acceleration of wound healing, the stimulation of reticular hematopoietic organ and endocrine organ, and the enhancement of antibody formation.

However, the fact that Platonin does not almost possess any toxicity and side-effect and shows an excellent immunomodulating action, particularly in oral administration, which was not known in the prior art, for the first time, has been found out by the present inventor.

That is, in the present invention, there has been found the useful and excellent pharmacological properties of Platonin as follows: Platonin possesses such a typical immunomodulating action that it shows an immunological activating effect when the immunological function is lowered, and it shows an immunosuppressive effect when the immunological function is enhanced, and it has no influence on the normal immunological function. On the other hand, Platonin does not have side-effects such as cytotoxicity (e.g. granulocytopenia), vomiting, nausea, pyrexia, rash and myasthenia, which are common abuses encountered with conventional immunomodulators, and rather has such a desirable characteristic that it maintains the normal function of cells. Thus Platonin is an ideal immunomodulator. A consecutive administration of it for a long period of time is possible and therefore Platonin is extremely effective for treatment of autoimmune diseases, particularly rheumatoid arthritis and nephritis.

Moreover, it has been found that Platonin exhibits an excellent pharmacological activity in a surprisingly trace dose in oral administration, e.g. 1/1,000 to 1/10,000 of that with conventional immunomodulators.

The above-mentioned advantages make Platonin a medicament being easy to handle as compared with conventional immunomodulators. Generally oral administration is desirable in case of rheumatoid arthritis as compared with other diseases, since rheumatoid arthritic patients are difficult to go to hospital regularly.

Thus, an immunomodulator containing Platonin as an effective ingredient contributes greatly to the prevention and treatment of all immune diseases, particularly the treatment of rheumatoid arthritis.

Furthermore, in the present invention, it has been found that the homologues of Platonin in which the n-heptyl group of Platonin is changed to other alkyl groups having 1 to 15 carbon atoms possess an excellent immunomodulating property equal to that of Platonin.

The group R in the general formula (I) is an straight or brnached alkyl group having 1 to 15 carbon atoms. Examples of the group R include methyl, ethyl, n-propyl, isopropyl, n-butyl, isobutyl, sec-butyl, tert-butyl, n-pentyl, isopentyl, sec-pentyl, neopentyl, tert-pentyl, n-hexyl, isohexyl, sec-hexyl, neohexyl, tert-hexyl, n-heptyl, 5-methylhexyl, octyl, nonyl, decyl, undecyl, dodecyl, tridecyl, tetradecyl and pentadecyl. Examples of X in the general formula (I) include halogen atoms such as chlorine, bromine and iodine, and the residual groups of perchloric acid, nitric acid and organic acids such as p-toluenesulfonic acid, nicotinic acid and orotic acid.

The preferred compounds are those of the general formula (I) wherein R is heptyl or octyl, particularly n-heptyl or n-octyl, and X is iodine.

The preferred indications to which the compounds of the general formula (I) are applied are autoimmune diseases including rheumatoid arthritis, systemic lupus erythematosus (SLE), nephritis and autoimmune hemolytic anemia; immediate type or delayed type allergy; and immunologic deficiency diseases including malignant tumor and severe infectious disease. The most preferred indications are rheumatoid arthritis and nephritis.

The pharmaceutical composition containing the compound of the general formula (I) as an effective ingredient according to the present invention shows an excellent immunomodulating action in an extremely low adult-dosage of about 10 to about 500 μg./one time on the basis of the amount of the effective ingredient. The preferred dosage is from 50 to 100 μg./1 or 2 days.

The pharmaceutical composition of the present invention is preferably administered orally to show a sufficient activity. In that case, it can be used in a variety of preparation forms such as tablet, capsule, powder, granule and liquid. Further, the pharmaceutical composition of the present invention is also used in other preparation forms such as collunarium and suppository.

The preparation of the pharmaceutical composition of the present invention can be conducted in any usual manner using conventional pharmaceutically acceptable carriers with no specific limitations. Examples of such carriers include binders, solid diluents, liquid diluents, fillers, and the like, e.g. lactose, starch, sucrose fatty acid ester, microcrystalline cellulose, hydroxypropyl methyl cellulose, hydroxypropyl methyl cellulose phthalate, glycerin, triglyceride, diglyceride, monoglyceride, sugar, sodium citrate, sodium benzoate, magnesium stearate, silicon dioxide, talc, physiological salt solution and distilled water.

The compounds of the general formula (I) are prepared in the following manner:

2,4-Dimethylthiazole (b.p. 146° to 147° C.), which is readily prepared from monochloroacetone and thioacetamide, is heated at about 170° C. with an alkyl iodide having 1 to 15 carbon atoms to give 3-alkyl-2,4-dimethylthiazolium iodide. This compound is heated at 140° to 145° C. with ethyl orthoformate and acetic anhydride, and the resulting crude product is recrystallized from an appropriate solvent, e.g. ethanol, to give the desired compound, 4,4'-dimethyl-3,3'-dialkyl-8-[2-(4-methyl-3-alkylthiazole)]-2,2'-dicarbocyanine diiodide.

The diiodide compound thus obtained is converted to dichloride, dibromide and di-p-toluenesulfonate compounds by treatment with silver chloride, silver bromide and p-toluenesulfonic acid solutions, respectively. And the diperchloric acid, dinitric acid and diorganic acid salt compounds are obtained by the treatment of p-toluenesulfonate compound with perchloric acid, nitric acid and organic acid solutions, respectively.

As to some of the compounds of the formula (I), the melting points thereof are shown in Table 1.

TABLE 1

| Compound No. | Formula (I) R | Formula (I) X | m.p. (°C.) |
|---|---|---|---|
| 1 | Methyl | I | 264 to 266 |
| 2 | n-Butyl | I | 219 to 222 |
| 3 | n-Heptyl | I | 202 to 204 |
| 4 | " | Cl | 150 to 155 |
| 5 | " | Br | 118 to 120 |
| 6 | " | ClO$_4$ | 210 to 213 |
| 7 | " | nicotinate | 132 to 133 |
| 8 | " | orotate | 125 to 126 |
| 9 | n-Octyl | I | 203 to 205 |
| 10 | n-Dodecyl | I | 198 to 200 |

The present invention is more particularly described and explained by means of the following Examples. These Examples are intended to illustrate the invention and not be construed to limit the scope of the invention. It is to be understood that various changes and modifications may be made in the invention without departing from the spirit and scope thereof.

EXAMPLE 1

[Inhibition of adjuvant arthritis]

Five SD rats 7 to 8 weeks old weighing about 150 g. were used as one group. A dispersion of mycobacterium butyricium in liquid parrafin in a concentration of 12 mg./ml. was injected intracutaneously into the footpad of the right hind foot in a dose of 0.05 ml./rat to cause an adjuvant arthritis (AA). For 30 days after the injection of the adjuvant, the volume of both hind feet was measured by a mercury plethysmography and AA was estimated from the obtained measurements.

(1) Preventive effect

Figure 2:
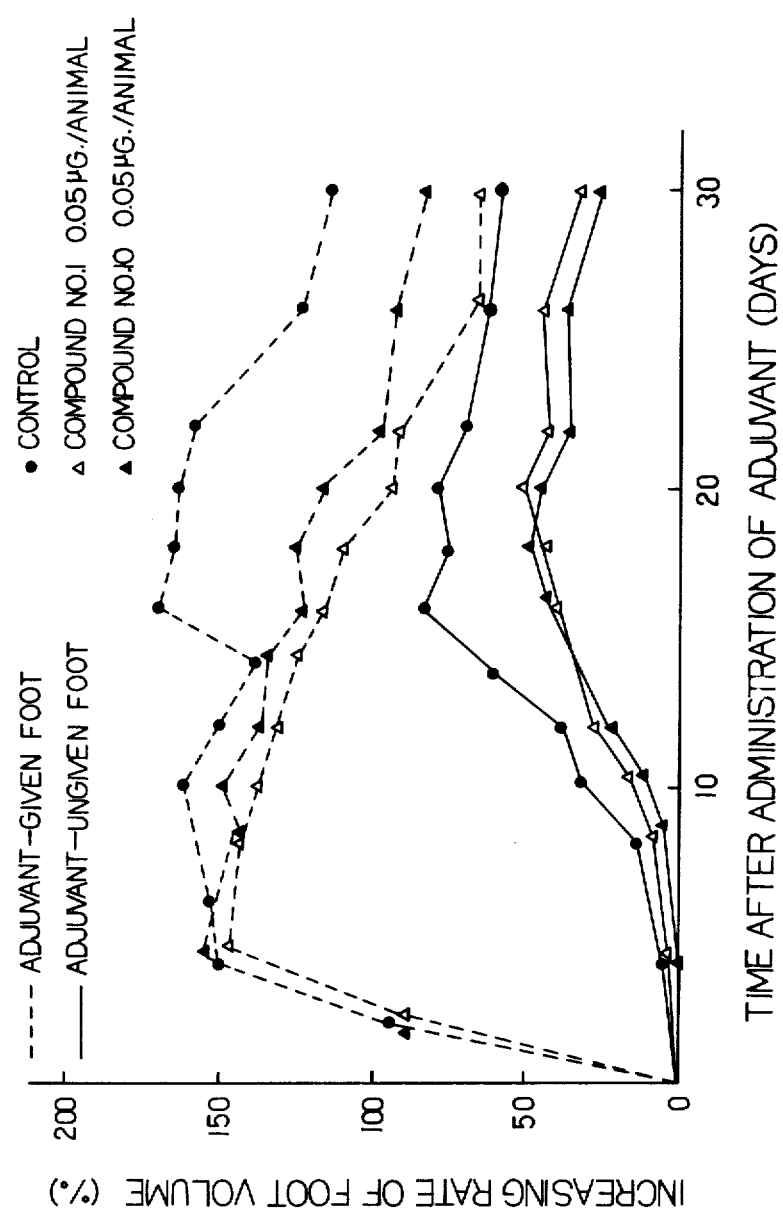

With respect to Compound Nos. 1, 3 and 10, the preventive effect on AA was examined. The oral administration of the compound to be tested was begun at the same time as the administration of the adjuvant and continued for 30 days once a day. The results are shown in FIGS. 1 and 2. The same test was carried out with D-penicillamine and Levamisole. The results are shown in FIG. 3.

Figure 3:
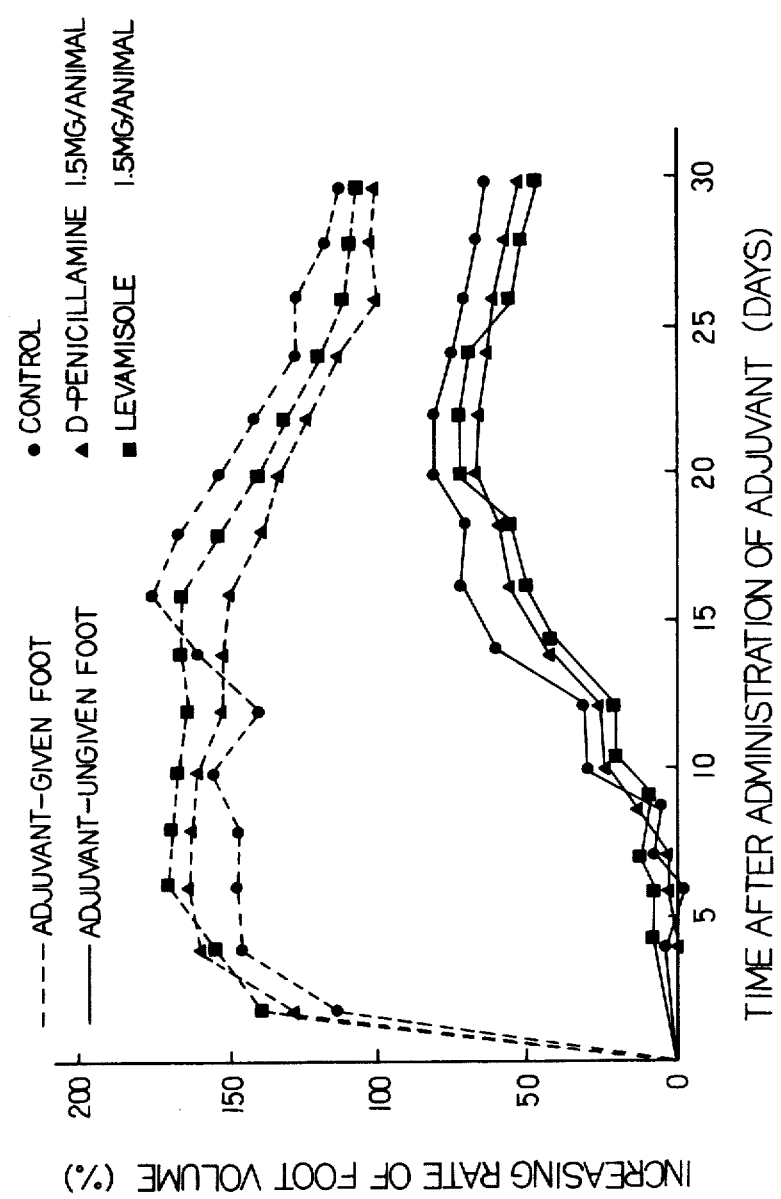
FIG. 3 is a graph showing the preventive effect of D-penicillamine and Levamisole on adjuvant arthritis in rat.

The results of FIGS. 1, 2 and 3 reveal that the instant compounds (I) (Compound Nos. 1, 3 and 10) inhibit AA at a lower dose of 0.05 μg./animal, while D-penicillamine and Levamisole do not inhibit AA even at a higher dose of 1.5 mg./animal. Particularly, Compound No. 3 (Platonin) inhibited AA at a much lower dose of 0.005 μg./animal, as shown in FIG. 1.

(2) Therapeutic effect

Figure 4:
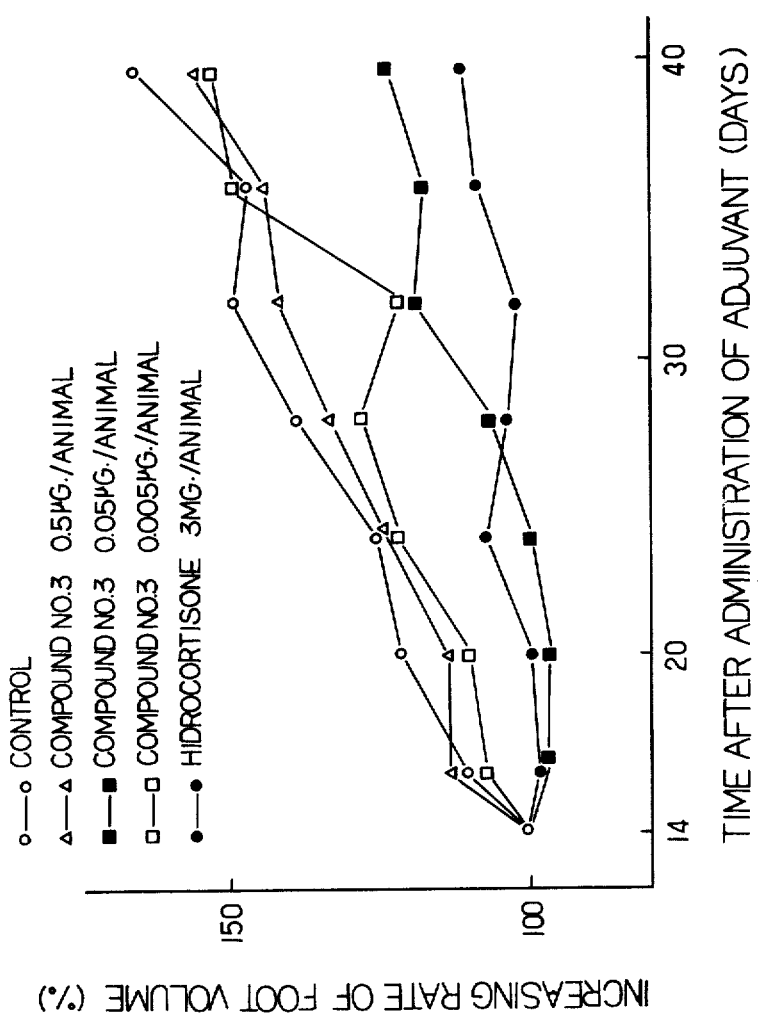
FIGS. 4 and 5 are graphs showing the therapeutic effect of the instant immunomodulator and hydrocortisone on adjuvant arthritis in rat.
Figure 5:
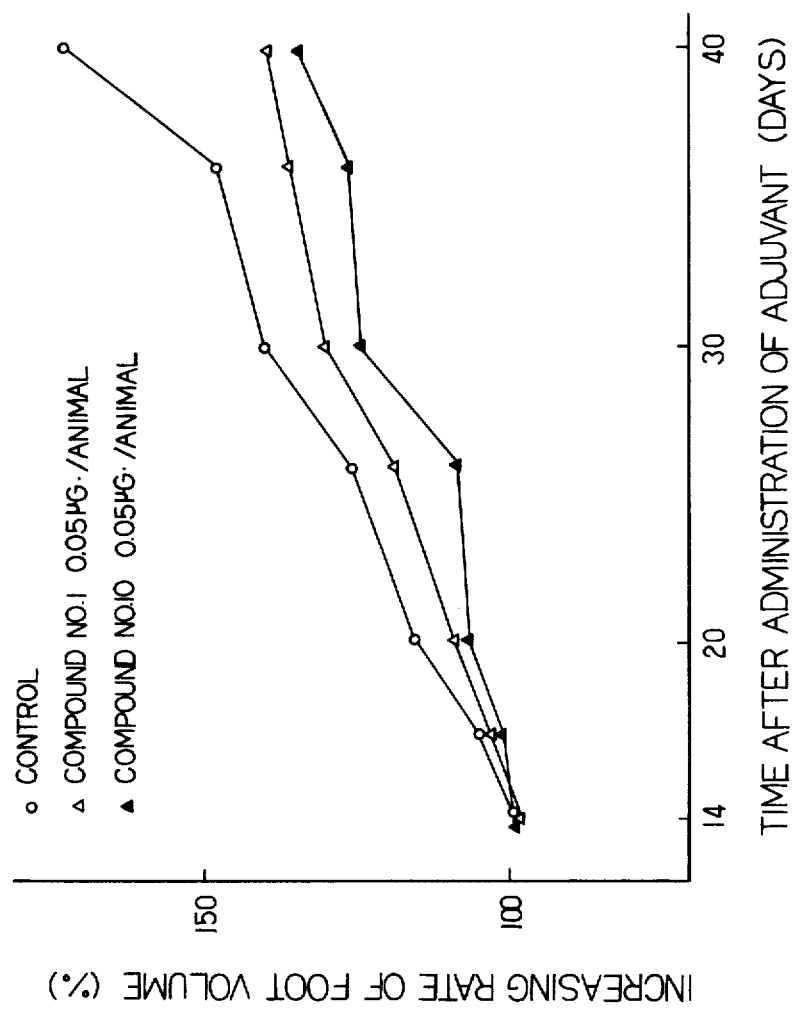

With respect to Compound Nos. 1, 3 and 10, the therapeutic effect on AA was examined. The oral administration of the compound to be tested was begun from the 14th day after the administration of the adjuvant and continued for 40 days once a day. The results are shown in FIGS. 4 and 5. The same test was carried out with hydrocortisone. The results are also shown in FIG. 4.

The results of FIGS. 4 and 5 reveal that the instant compounds (I) inhibit AA in a lower dose of 0.05 μg./animal but the instant compounds (I) do not inhibit AA in a dose of more than about 1 μg./animal. Those facts show that the instant compounds (I) has an optimum dosage.

(3) Change in body weight

During the test of the preventive effect on AA as described in the above (1), the body weight of each rat was measured on 1st, 10th, 20th, and 30th day. The results are shown in FIGS. 6 and 7.

Figure 6:
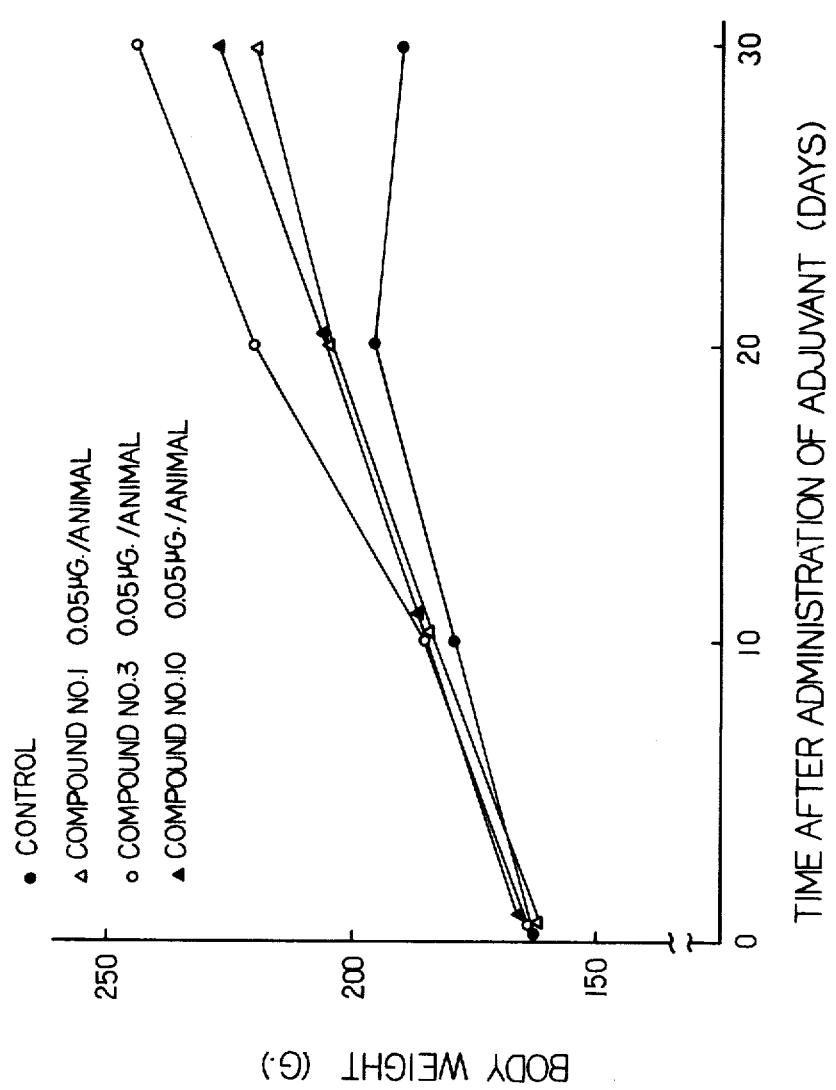
FIG. 6 is a graph showing the effect of the instant immunomodulator on the body weight of rat with adjuvant arthritis.
Figure 7:
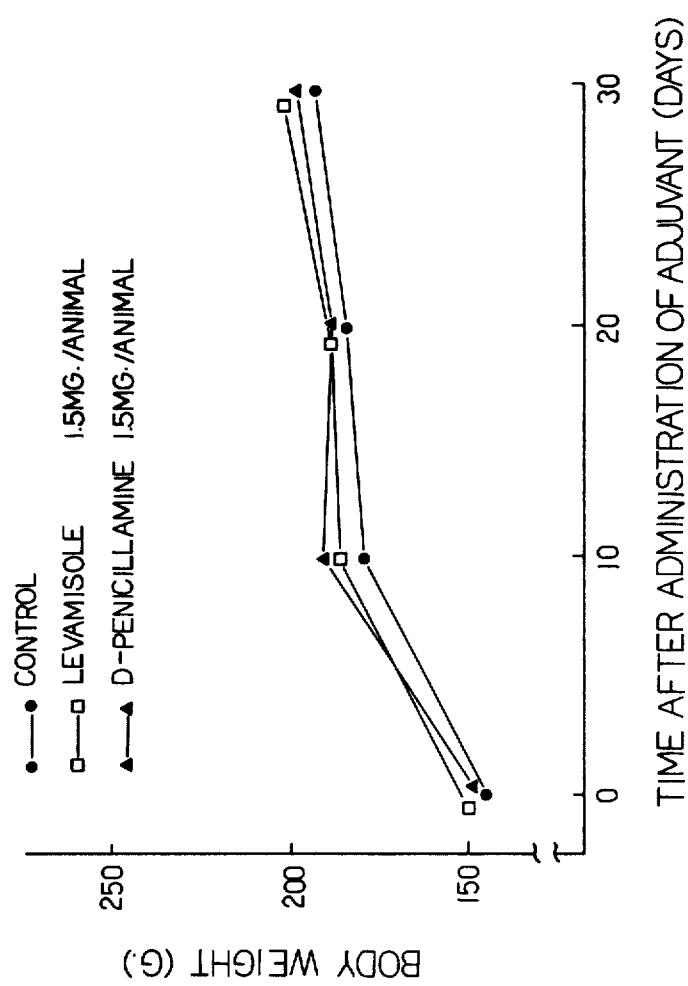
FIG. 7 is a graph showing the effect of D-penicillamine and Levamisole on the body weight of rat with adjuvant arthritis.

As shown in FIGS. 6 and 7, there was no significant difference between the change in body weight with administration of D-penicillamine or Levamisole and that in Control. On the contrary, in case of administration of the instant compounds (I) in a dose of 0.05 μg./animal, there was clearly observed an increase in body weight as compared with Control, nevertheless the reduction of swelling in foot, and in addition there was observed an outstanding systemic improvement of diseases.

EXAMPLE 2

[Effect on carrageenan-induced edema]

Five SD rats 7 to 8 weeks old weighing about 150 g. were used as one group. A 1% dispersion of carrageenan was injected intracutaneously into the foot pad of the right hind foot in a dose of 0.1 ml./rat. For 6 hours after the injection, the volume of the foot subjected to the injection was measured by a mercury plethysmography and the carrageenan-induced edema was estimated from the obtained measurements. Compound No. 3 was orally administered 30 minutes before the injection of the carrageenan dispersion. The results are shown in FIG. 8.

Figure 8:
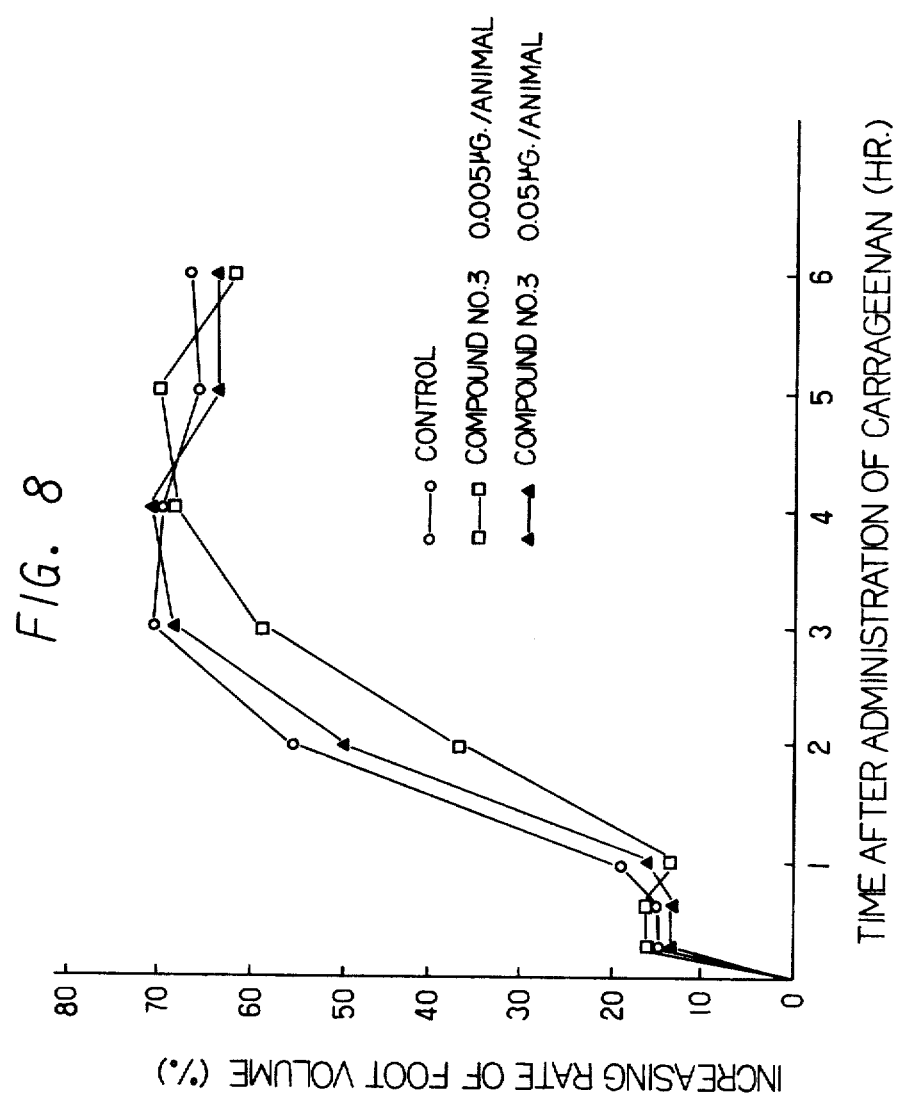
FIG. 8 is a graph showing the effect of the instant immunomodulator on carrageenan-induced edema in rat.

As shown in FIG. 8, Compound No. 3 did not show anti-inflammatory action on the carrageenan-induced edema in a dose of 0.005 to 0.05 μg./animal. From this fact, it is presumed that the pharmacological property of the instant compounds (I) is revealed by immunomodulating action rather than anti-inflammatory action.

EXAMPLE 3

[Effect on PFC response in splenocyte of mice]

Employing the splenocytes of Balb/c mice, the effects of Compound Nos. 1, 2, 3, 9 and 10 on PFC (plaque forming cells) response to SRBC (sheep red blood cells) were examined.

Figure 9:
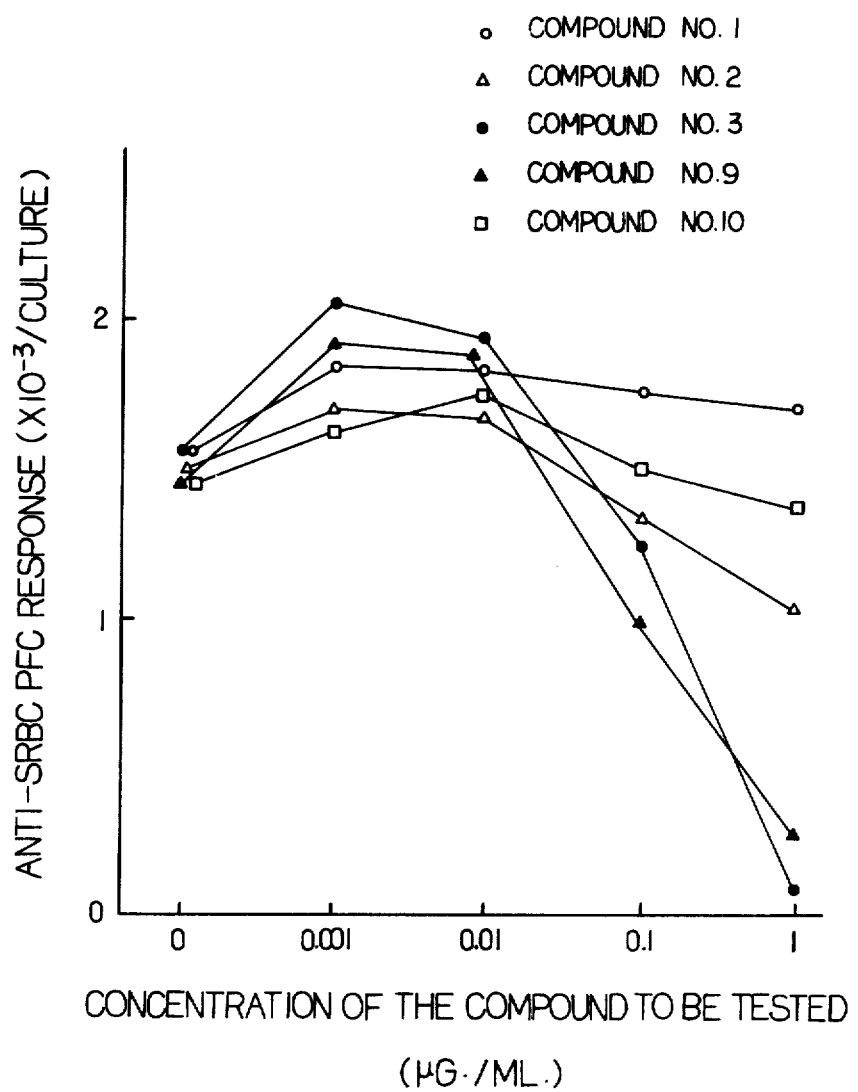
FIG. 9 is a graph showing the effect of the instant immunomodulator on PFC response in splenocyte of Balb/c mice.

There were incuvated $1 \times 10^7$ splenocytes of Balb/c mice together with SRBC and the compound to be tested in RPMI-1640 medium containing 10% of bovine fetal serum in a $CO_2$-incubator kept at 37° C. for 4 days according to the Marbrook method. The number of the direct PFC was measured according to the method of Jerne (cf., Science, Vol. 140, p.405, 1963). The results are shown in FIG. 9. With respect to the anti-SRBC PFC response, the instant compounds (I) showed a biphasic action, i.e. an activation in a lower dose and an inhibition in a higher dose.

EXAMPLE 4

[Effect on blastogenesis in splenocyte of mice]

Employing the splenocytes of Balb/c mice, the effects of Compound Nos. 1, 2, 3, 9 and 10 on the blastogenesis stimulated by LPS as mitogen were examined.

Figure 10:
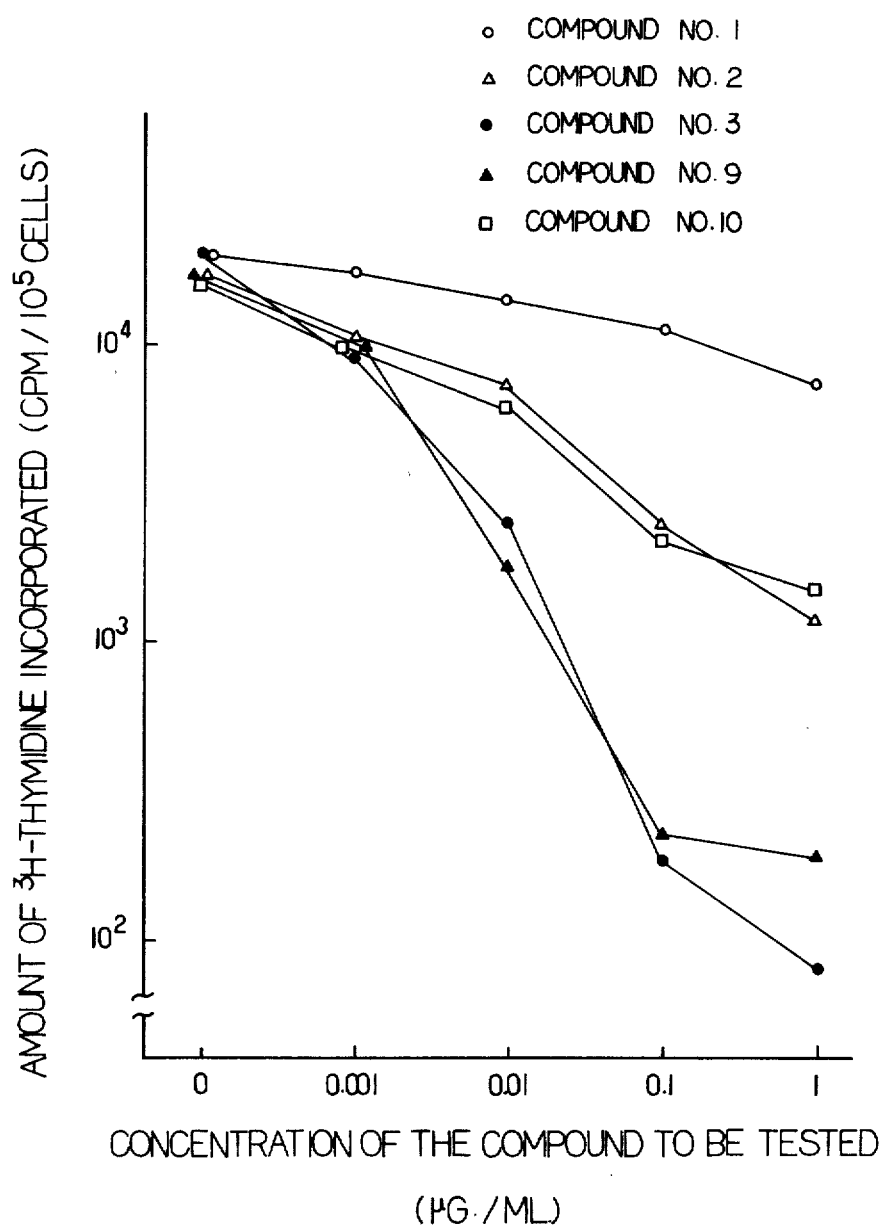
FIG. 10 is a graph showing the effect of the instant immunomodulator on blastogenesis in splenocyte of Balb/c mice.

There were incuvated $1 \times 10^5$ splenocytes of Balb/c mice together with the mitogen and the compound to be tested in RPMI-1640 medium containing 10% of bovine fetal serum on a microculture plate in a $CO_2$-incubator for 48 hours. Thereto was added 0.5 microcurie of $^3H$-thymidine ($^3H$-TdR). After additional incubation for 18 hours, the cells were collected by an auto cell harvester (Lab Mash: registered trademark) and the radioactivity of $^3H$-TdR incorporated into the cells was measured. The results are shown in FIG. 10. The instant compounds (I) outstandingly inhibited blastogenesis stimulated by LPS, B-cell mitogen, in a concentration of 20 μg./ml.

EXAMPLE 5

[Acute toxicity]

Eight male ddY mice 5 to 6 weeks old weighing 25 to 30 g. were used as one group. A 5% suspension of the compound to be tested in gum arabic was administered intraperitoneally, intravenously or orally using a stomach tube. The animals were kept under observation for 7 days. The numbers of dead animals were counted and the $LD_{50}$ values were calculated by the Van der Wärden method. The results are shown in Table 2.

TABLE 2

| Compound No. | $LD_{50}$ (mg./kg. body weight) | | |
|---|---|---|---|
| | i.p. | i.v. | p.o. |
| 1 | 23.4 | 6.25 | >1,400 |
| 2 | 51.0 | 8.50 | >1,400 |
| 3 | 100 | 12.0 | >1,400 |
| 9 | 120 | 13.5 | >1,400 |
| 10 | 300 | 45.2 | >1,400 |

The $LD_{50}$ values of the instant compounds (I) were 23.4 to 300 mg./kg. in i.p. and more than 1.4 g./kg. in p.o. As considered that the instant compounds (I) are effective in a dose of 0.05 μg./animal in inhibition of the adjuvant arthritis as mentioned in Example 1, it is clear that the instant compounds (I) are immunomodulators having a markedly wide safety margin.

EXAMPLE 6

[Clinical test]

(1) Case 1

A patient 47 years old was treated with Compound No. 3. He was attacked with rheumatoid polyarthritis 3 years ago and complained of a violent pain at right articulatio coxae. The condition was not improved even by injecting 25 mg. of Shiozol (registered trademark) twice a week.

To the above patient was orally administered Compound No. 3 in a dosage of 50 μg. once a day before the meal. After 5 days, the stiffness in the morning and the systemic malaise were relieved and the inflammation at wrist articulatio coxae and the violent pain were almost removed. In the morning of the seventh day, the patient could arise from a sickbed and go down the stairs with ease. Thus, the instant immunomodulator showed an excellent therapeutic effect with no side-effect.

(2) Case 2

A patient 57 years old was treated with Compound No. 3. He was attacked with rheumatoid polyarthritis 8 years ago. The condition took a turn for the worse even by the treatment using a suppository of Shiozol and that of Indometacin (registered trademark). He suffered from gastric ulcer, urticaria and diarrhea due to the side-effect of the medicines used. He complained continuously of a pain everyday and was confined to his bed or could not walk without crutches.

To the above patient was orally administered Compound No. 3 in a dosage of 100 μg. once a day before the meal. After 3 days, the systemic malaise and the stiffness in the norming were relieved. After 5 days, the inflammation at the joints was relieved and there was no necessity for administering the suppository of Indometacin and the patient became to sleep well. After 7 days, Compound No. 3 was orally administered twice a week. After 3 weeks, the swelling (hydrocele) at the joints was improved and the patient became to be able to walk. No side-effect was observed.

EXAMPLE 7

Employing Compound Nos. 1 to 10 as an effective ingredient, there were prepared immunomodulators in a variety of preparation forms as in the followings:

(1) Tablet

Tablets having the following composition were prepared in a usual manner.

| Component | mg./tablet |
| --- | --- |
| Effective ingredient | 0.05 |
| Lactose | 79.95 |
| Corn starch | 62.50 |
| Sucrose fatty acid ester | 7.50 |
| Total | 150 |

In case of gastric coating tablets, the above tablets were further subjected to a 5% by weight coating of Tc-5 (hydroxypropyl methyl cellulose made by Shin-Etsu Chemical Co., Ltd.), followed by application of a sugar coating. In case of enteric coating tablets, the above tablets were further subjected to a 10% by weight coating of HP-55 (hydroxypropyl methyl cellulose phthalate made by Shin-Etsu Chemical Co., Ltd.), followed by application of sugar coating.

(2) Capsule

Capsules having the following composition were prepared in a usual manner.

| Component | mg./capsule |
| --- | --- |
| Effective ingredient | 0.05 |
| Lactose | 146.95 |
| Sucrose fatty acid ester | 3.00 |
| Total | 150 |

(3) Powder

A powder having the following composition was prepared in a usual manner.

| Component | mg./wrapper |
| --- | --- |
| Effective ingredient | 0.05 |
| Lactose | 499.95 |
| Total | 500 |

(4) Suppository

Two kinds of suppositories having the following compositions were prepared in a usual manner.

| Component | mg./suppository |
| --- | --- |
| Suppository A | |
| Effective ingredient | 0.05 |
| Polyethylene glycol (#1,000) | 1,440 |
| Polyethylene glycol (#4,000) | 59.95 |
| Total | 1,500 |
| Suppository B | |
| Effective ingredient | 0.05 |
| Witepsol H-15* | 1,280 |
| Witepsol H-80* | 319.95 |
| Total | 1,600 |

*Mixture of triglyceride and monoglyceride made by Dynamit Novel, Chemicals, Witepsol: registered trademark.

(5) Syrup

A syrup (dosage/one time: 50 μg./5 ml.) having the following composition was prepared in a usual manner.

| Component | Content/100 ml. |
| --- | --- |
| Effective ingredient | 1 mg. |
| Sugar | 60 g. |
| Glycerin | 10 g. |
| Sodium citrate | 0.1 g. |
| Sodium benzoate | 0.3 g. |
| Saccharin sodium salt | 0.1 g. |
| Distilled water | Appropriate amount |

What is claimed is:

1. A method of treating an immune disease comprising administering an immunomodulating effective amount of a trithiazole pentamethine cyanine derivative of the general formula (I)

$$\underset{H_3C}{\overset{S}{\underset{\overset{\oplus}{N}}{\bigvee}}}-CH=CH-\underset{\underset{R}{|}}{\overset{\overset{CH_3}{\underset{|}{\overset{}{\diagup}}}}{\overset{\oplus}{\underset{}{C}}}}=CH-CH=\underset{\underset{R}{|}}{\overset{S}{\underset{N}{\bigvee}}}\overset{CH_3}{\phantom{|}} \quad .2X^{\ominus} \qquad (I)$$

wherein R is an alkyl group having 1 to 15 carbon atoms, and X is a halogen atom, or a residual group of perchloric acid, nitric acid or an organic acid, to a patient having an immune disease.

2. The method of claim 1, wherein R in the compound of the formula (I) is a heptyl group.

3. The method of claim 2, wherein the heptyl group is n-heptyl.

4. The method of claim 2 or 3, wherein X is iodine.

5. The method of claim 1, wherein R in the compound of the formula (I) is an octyl group.

6. The method of claim 5 wherein the octyl group is n-octyl.

7. The method of claim 5 or 6 wherein X is iodine.

8. The method of claim 1, the indication for which is rheumatoid arthritis.

9. The method of claim 1, wherein the compound of formula (I) is in a preparation form suitable for oral administration.

* * * * *